(12) United States Patent
Poulter et al.

(10) Patent No.: US 10,087,138 B2
(45) Date of Patent: Oct. 2, 2018

(54) ANTICONVULSANT COMPOUNDS

(71) Applicant: OWEN-BARRY PHARMACEUTICALS INC., London (CA)

(72) Inventors: Michael Poulter, London (CA); Tony Durst, Ottawa (CA)

(73) Assignee: OWEN-BARRY PHARMACEUTICALS INC., London, Ontario (CA)

( * ) Notice: Subject to any disclaimer, the term of this patent is extended or adjusted under 35 U.S.C. 154(b) by 0 days.

(21) Appl. No.: 15/879,706

(22) Filed: Jan. 25, 2018

(65) Prior Publication Data

US 2018/0148405 A1 May 31, 2018

Related U.S. Application Data

(63) Continuation of application No. 15/174,099, filed on Jun. 6, 2016.

(60) Provisional application No. 62/171,508, filed on Jun. 5, 2015.

(51) Int. Cl.
C07C 255/31 (2006.01)

(52) U.S. Cl.
CPC ........ *C07C 255/31* (2013.01); *C07C 2601/02* (2017.05); *C07C 2601/16* (2017.05)

(58) Field of Classification Search
None
See application file for complete search history.

(56) References Cited

U.S. PATENT DOCUMENTS

| 4,847,073 A | 7/1989 | Cleary et al. |
| 7,399,888 B2 | 7/2008 | Rahman et al. |
| 2014/0221682 A1 | 8/2014 | Rahman et al. |
| 2015/0148417 A1 | 5/2015 | Rahman et al. |

OTHER PUBLICATIONS

Rouillard, M. et al. H NMR Utilization of Through-space Effects II—conformation of Dienic Ketones. Organic Magnetic Resonance. Jun. 1981, vol. 16, No. 2, pp. 94-97.

Tomioka, K. and Koga, K. Conjugate Addition Reation of Trimethylsilylacetonitrile with -Unsaturated Carbonyl Compounds, Synthetic Studies Toward Sesbanimide, Tetrahedron Letters, Jan. 1984, vol. 25, Issue 15, pp. 1599-1600.

Ishii, K.et al. Photochemical Reactions of a,B-Unsaturated—Epoxy Ketones and Nitriles in the Presence of Armine, J. Chem. Soc. Perkin Trans. 1990, vol. 4, pp. 855-861.

Kurihara, T. et al. Allylic Rearrangement of Cynaophosphate. II Synthesis of—Cyano—unsaturated Ketones. Chem. Pharm. Bull. 1986, vol. 34, No. 7, pp. 2747-2753.

Magnus, P. et al. Direct Conversion of—Unsaturated Nitriles into Cyuanohydrins using Mn(dpm) Catalyst, Dioxygen and Phenlsilane. Tetrahedron Letters, Jun. 2001, vol. 42, pp. 4127-4129.

Brindani, N. et al. Organocatalytic, Asymmetric Eliminative [4+2] Cycloaddition of Allylidene Malononitriles with Enals; Rapid Entry to Cyclohexadiene-Embedding Linear and Angular Polycycles. Angewandte Communications. May 2015, vol. 54, pp. 7389-7390.

*Primary Examiner* — Bong-Sook Baek

(57) ABSTRACT

The present application relates to compounds and methods for reducing the severity of convulsant activity, or epileptic seizures.

12 Claims, 2 Drawing Sheets

ANTICONVULSANT COMPOUNDS

FIELD OF THE INVENTION

The present invention relates to compounds with anticonvulsant and pain activity. These compounds are useful in modulating voltage-gated sodium channel activity and are thus useful in the treatment of epilepsy and chronic or acute pain.

BACKGROUND

Anti-convulsant compounds are presently in wide use in the treatment of a variety of conditions and diseases, including epilepsy. Epilepsy is a neurological condition which affects the nervous system and causes individuals with epilepsy to suffer from seizures. These seizures are caused by disruptions in the electrical communication between neurons in the brain. Epilepsy can be conceptualized as brain activity that is inappropriately synchronous. Seizures are often seen in electro encephalograms (EEGs) as high amplitude neural discharges that occur across brain regions. This brain activity is accompanied by behavioral disturbances that include loss of balance, jerking muscle movement, visual disturbances, and loss of consciousness. It is estimated that about 0.5% of the world's population has some form of epilepsy. Epilepsy is a lifelong condition, has a very low reversion rate, and is only rarely fatal. Persons with uncontrolled epilepsy are often under or un-employed.

The combination of all these factors makes epilepsy among the most expensive health care burdens in the world. In North America alone, the cost of epilepsy due to direct health care costs and lost economic activity is estimated to be in the billions of dollars each year. There is no known cure for epilepsy.

The control of epileptic seizures is an unmet medical challenge. Current medications control seizures by targeting a number of sites in the central nervous system (CNS). These drugs, while effective, often produce undesirable side effects that reduce compliance and therefor efficacy. Reportedly, nearly 30% of individuals with epilepsy do not respond to any current therapies, including both drug and brain stimulation therapies. Accordingly, there is a need to develop novel anticonvulsants in order to provide effective alternatives for these individuals.

As well the management of acute and chronic pain is an ongoing problem. There are millions of people living with various forms of chronic pain. Blocking sodium channel function is one of many treatments.

SUMMARY OF THE INVENTION

In one embodiment, the present disclosure includes a method for eliminating or reducing the severity of convulsant activity or epileptic seizures by administering to a subject a therapeutically effective amount of an E and Z mixture of a compound represented by the formula (I).

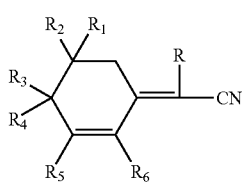

(I)

Where R=H, $CH_3$, $C_2$ to $C_6$ (linear or branched), $cC_3H_5$, $cC_5H_9$, $cC_6H_{11}$, $CH=CH_2$, or $CH_2Ar$
$R_1=R_2=$H or $CH_3$
$R_3=R_4=$H or $CH_3$
$R_5=$H, $CH_3$, $OCH_3$, $OCH_2Ar$, Cl, or Br
$R_6=$H or $CH_3$ In another embodiment, the method comprises administering to a subject a therapeutically effective amount of a compound represented by the following chemical formula that is a mixture of E and Z isomers.

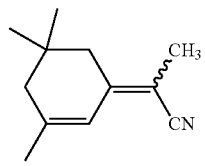

In yet another embodiment, the method comprises administering to a subject a therapeutically effective amount of the Z isomer of a compound represented by the following chemical formula.

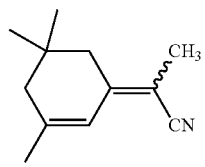

In another aspect, the present invention relates to a pharmaceutical composition including a compound represented by the formula (I), or a pharmaceutically acceptable salt or solvate thereof, together with a pharmaceutically acceptable excipient.

In another embodiment, the composition includes a compound represented by the following chemical formula and is a mixture of E and Z isomers.

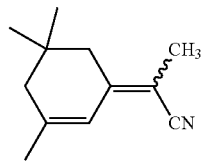

In yet another embodiment, the composition includes the Z isomer of a compound represented by the following chemical formula.

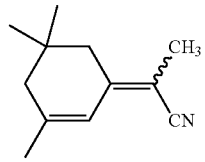

Further features of the invention will be described or will become apparent in the course of the following detailed description.

BRIEF DESCRIPTION OF THE DRAWINGS

In order that the invention may be more clearly understood, preferred embodiments thereof will now be described in detail by way of example, with reference to the accompanying drawings, in which.

DESCRIPTION OF PREFERRED EMBODIMENTS

Figure 1:
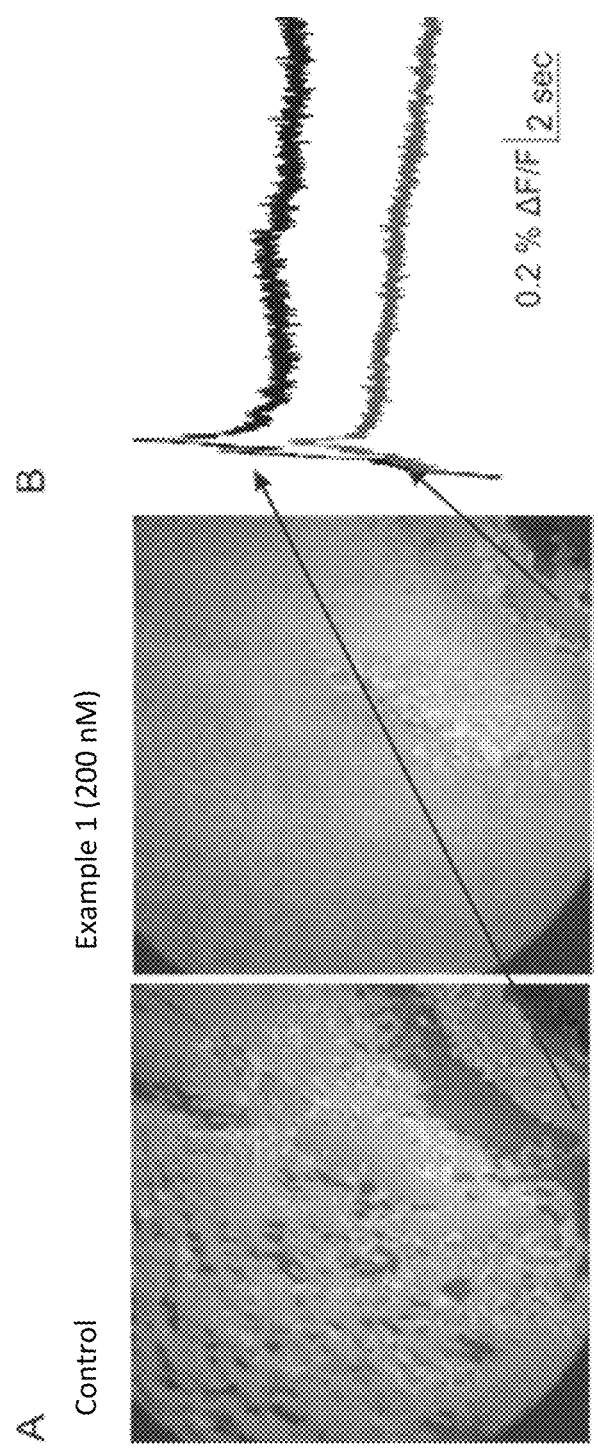
FIG. 1 is a side-by-side comparison of brain activity in a control sample and in the presence of a preferred compound according to the present invention.

It has been found that certain compounds, described herein, are voltage-gated sodium channel inhibitors with anti-convulsive activity. Voltage-gated sodium channels are found in the neurons of the central and peripheral nervous system and are responsible for generating the rapid upstroke of the action potential. They are essential to the nervous system's ability to initiate and propagate electrical signals.

The present invention provides a compound represented by the following formula (I):

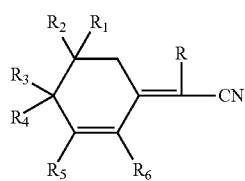

(I)

Where R=H, $CH_3$, $C_2$ to $C_6$ (linear or branched), $cC_3H_5$, $cC_5H_9$, $cC_6H_{11}$, $CH=CH_2$, or $CH_2Ar$
$R_1=R_2=H$ or $CH_3$
$R_3=R_4=H$ or $CH_3$
$R_5=H$, $CH_3$, $OCH_3$, $OCH_2Ar$, Cl, or Br
$R_6=H$ or $CH_3$ The above compounds are obtained as a mixture of E and Z isomers. Compounds of the invention containing one or more asymmetric carbon atoms can exist as two or more stereoisomers. Included within the scope of the invention are all stereoisomers of the compounds of the invention and mixtures of one or more thereof.

The compounds represented by formula (I), are inhibitors of voltage-gated sodium channel activity and are useful in the treatment of epileptic seizures and pain. Preferred compounds of the invention are those listed in the Examples below and the pharmaceutically acceptable salts and solvates thereof.

Epileptic seizures are caused by disturbances in the electrical activity of the brain. In particular, excessive electrical brain activity is a hallmark of an epileptic seizure. The electrical activity of the brain is primarily mediated by voltage-gated sodium channels. Thus, the dampening of voltage-gated sodium channel activity is a common target to control epileptic disturbances.

The present invention also provides a method for eliminating or reducing the severity of convulsant activity or epileptic seizures by administering to a subject a therapeutically effective amount of a compound represented by formula (I), or a pharmaceutically acceptable salt or solvate thereof, together with a pharmaceutically acceptable excipient.

The compounds of the present invention may be administered orally, parenterally, or topically. Topical administration is preferred for treatment of pain.

The compounds of the present invention may be prepared by the procedures described below. According to a first procedure, a preferred compound represented by formula (I) may be prepared according to the following methodology, as illustrated by the reaction sequence shown below:

An alpha-lithiated nitrile (1) is prepared by reaction of the corresponding nitrile with lithium diisopropylamide (LDA) in dry tetrahydrofuran (THF) at −78° C. under a nitrogen atmosphere. A cyclohex-2-en-1-one, for example isophorone (2), is added to a THF solution of the alpha lithio nitrile (1) at −78° C. The reaction mixture can be quenched by addition a 10% $NH_4Cl$ solution or allowed to warm to 0° C. prior to quenching; this results in the formation of the hydroxynitrile (3).

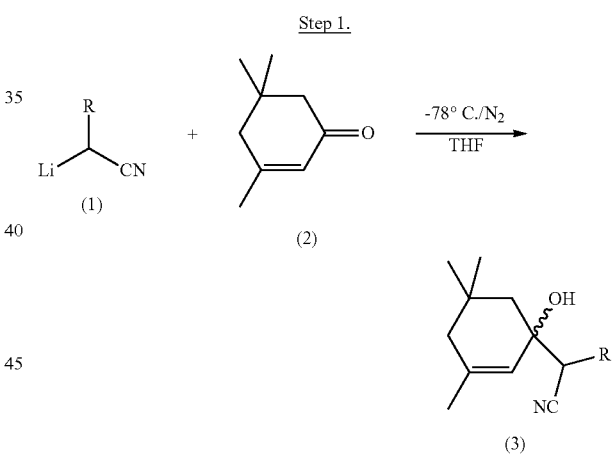

Step 1.

In the next step the purified hydroxynitrile (3) is stirred with a catalytic amount of acid in toluene or dichloromethane at room temperature. This induces the loss of water from (3) and results, typically, in the formation of up to five isomers (4a-4c, 5E, and 5Z).

Step 2.

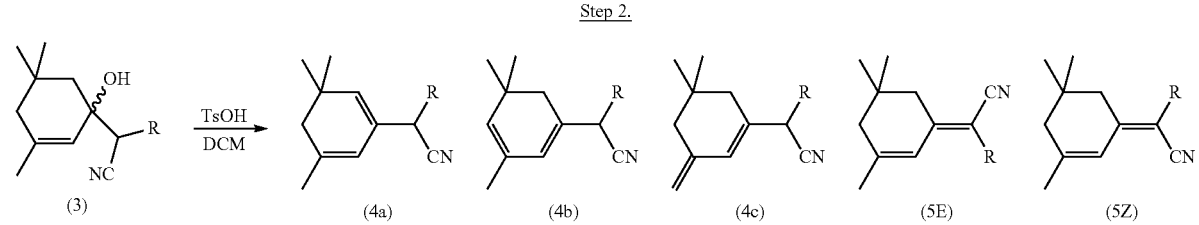

The mixture of isomers, when heated with ρ-toluenesulfonic (TsOH) acid in refluxing toluene, is converted cleanly to a mixture of the 5E and 5Z isomers.

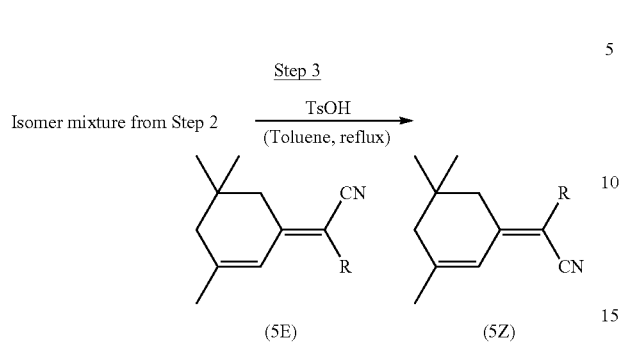

Step 3

The resulting mixture of stereoisomers may be separated, using known techniques for isolating individual enantiomers, including, for example, high pressure liquid chromatography. If enantiomers are present, Chiral HPLC may be used or the mixture may be reacted with a suitable optically active compound, thereby converting the mixture into a diastereomeric mixture, which may be separated using chromatography or fractional crystallization before converting one or both diastereoisomers back to the corresponding pure enantiomer by known techniques.

General Procedure for the Preparation of Diene Nitriles.

General Procedure 1: Coupling Reaction

The desired nitrile is added drop wise via syringe to a −78° C. solution of LDA (2M) in anhydrous THF (5-10 mL) under nitrogen atmosphere. This solution is stirred under these conditions for 5 min before adding the enone drop wise. The reaction mixture is kept at low temperature and quenched after 1 minute by addition of 10% aqueous NH₄Cl solution. Workup involves extraction with EtOAc (3×10 mL). The combined organic extracts are washed with water, dried over MgSO₄, filtered and concentrated in vacuo. The product is purified by gradient column chromatography using a gradient solvent system of EtOAc and hexanes.

General Procedure 2: Room Temperature Dehydration

The purified product obtained via general procedure 1 is stirred at room temperature in toluene (10-15 mL) containing a catalytic amount of PTSA until product formation is observed and the starting material has been consumed. The reaction mixture is quenched after 1 h with 10% aqueous NaHCO₃ and extracted with EtOAc (3×10 mL). The combined extracts are washed with water, dried (MgSO₄), filtered, and concentrated in vacuo. Purification by column chromatography affords a mixture of up to five isomers.

General Procedure 3: Isomerization to the E/Z Isomers

The mixture from General Procedure 2 is dissolved in toluene containing a catalytic amount of PTSA and refluxed for three hours, then quenched with 10% aqueous NaHCO₃ and extracted with EtOAc (3×10 mL). The combined extracts are washed with water, dried (MgSO4), filtered, and concentrated in vacuo. Purification by column chromatography affords the E/Z isomers of the desired compound.

Alternative Sequence.

The crude hydroxyl compound obtained via General procedure 1 may be subjected directly to dehydration in refluxing toluene (General Procedure 3).

Example 1

Preparation of the E/Z mixture of a preferred compound of the present invention is shown and described below.

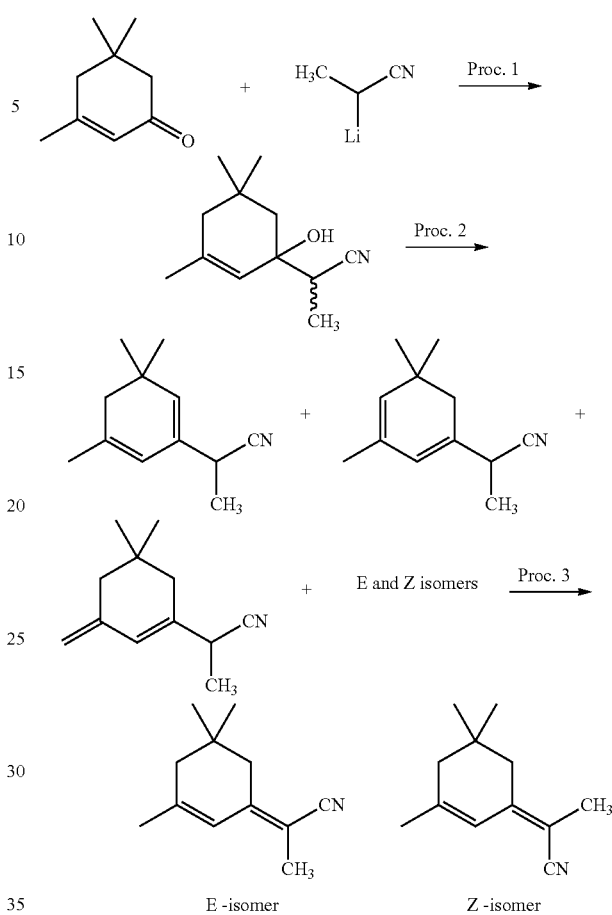

This compound is obtained following General Procedures 1, 2, and 3. General Procedure 1 is carried out starting with propionitrile (3.98 g, 72.4 mmol), in anhydrous THF (10 mL), LDA (36.2 mL, 72.35 mmol), and isophorone (5 g, 36.8 mmol) in anhydrous THF (5 mL). The crude product (6.50 g) is purified by gradient column chromatography to yield a pale yellow oil as product (5.53 g, 78%, Rf=0.33 in 4:1 Hexanes:EtOAc).

The semi-purified coupling product is dehydrated, according to General Procedure 2, to yield 5.20 g of a mixture of dienes, as a viscous oil (Rf=0.81 in 3:2 Hexanes:EtOAc) after column chromatography.

$^1$H NMR (400 MHz, CDCl$_3$) δ ppm 6.43 (d, J=1.4 Hz), 6.17 (dd, J=3.5, 1.8 Hz), 5.87-5.74 (m), 5.24-5.15 (m), 4.88 (d, J=19.2 Hz), 3.27 (dd, J=13.3, 6.8 Hz), 2.33 (d, J=1.4 Hz), 1.95 (ddd, J=34.6, 16.8, 3.0 Hz), 1.72 (d, J=1.6 Hz), 1.41 (dd, J=7.2, 0.7 Hz), 1.16-0.55 (m).

The above mixture of dienes is converted to a 5:4 mixture of E to Z dienes, according to General Procedure 3. Purification via column chromatography affords 5.20 g of a pale yellow oil (Rf=0.81 in 3:2 Hexanes:EtOAc). This material solidifies when stored in a freezer at −20 C.

$^1$H NMR (400 MHz, CDCl$_3$) δ ppm 6.45 (d, J=1.4 Hz), 6.18 (dd, J=3.0, 1.5 Hz), 2.34 (d, J=1.4 Hz), 2.09 (d, J=0.7 Hz), 1.98-1.89 (m), 1.84 (d, J=5.1 Hz), 0.93 (s).

The 5:4 mixture of E to Z dienes is determined by comparison of the integration of the peaks at 6.45 and 6.18 ppm due to the alkene hydrogens.

$^{13}$C NMR (100 MHz, CDCl$_3$) δ ppm 151.2, 149.9, 145.9, 144.0, 121.7, 121.0, 118.4, 99.3, 99.3, 45.2, 44.6, 43.2, 39.4, 31.2, 30.9, 28.2, 27.9, 24.6, 24.2, 15.5, 14.8.

The 5:4 E:Z diene mixture is recrystallized two consecutive times from hexanes at room temperature to yield 91% pure E isomer.

$^1$H NMR (400 MHz, CDCl$_3$) δ ppm 6.16 (dd, J=2.9, 1.4 Hz, 1H), 2.33 (d, J=1.3 Hz, 2H), 1.95 (s, 2H), 1.91 (s, 3H), 1.84 (s, 3H), 0.92 (s, 6H).

$^{13}$C NMR (100 MHz, CDCl$_3$) δ ppm 149.9, 145.9, 121.0, 118.5, 99.4, 45.3, 43.2, 31.3, 27.9, 24.6, 14.9.

Example 2

Preparation of the E/Z mixture of another preferred compound of the present invention (2-(3,5,5-trimethylcyclohex-2-en-1-ylidene)pentanenitrile), is shown and described below.

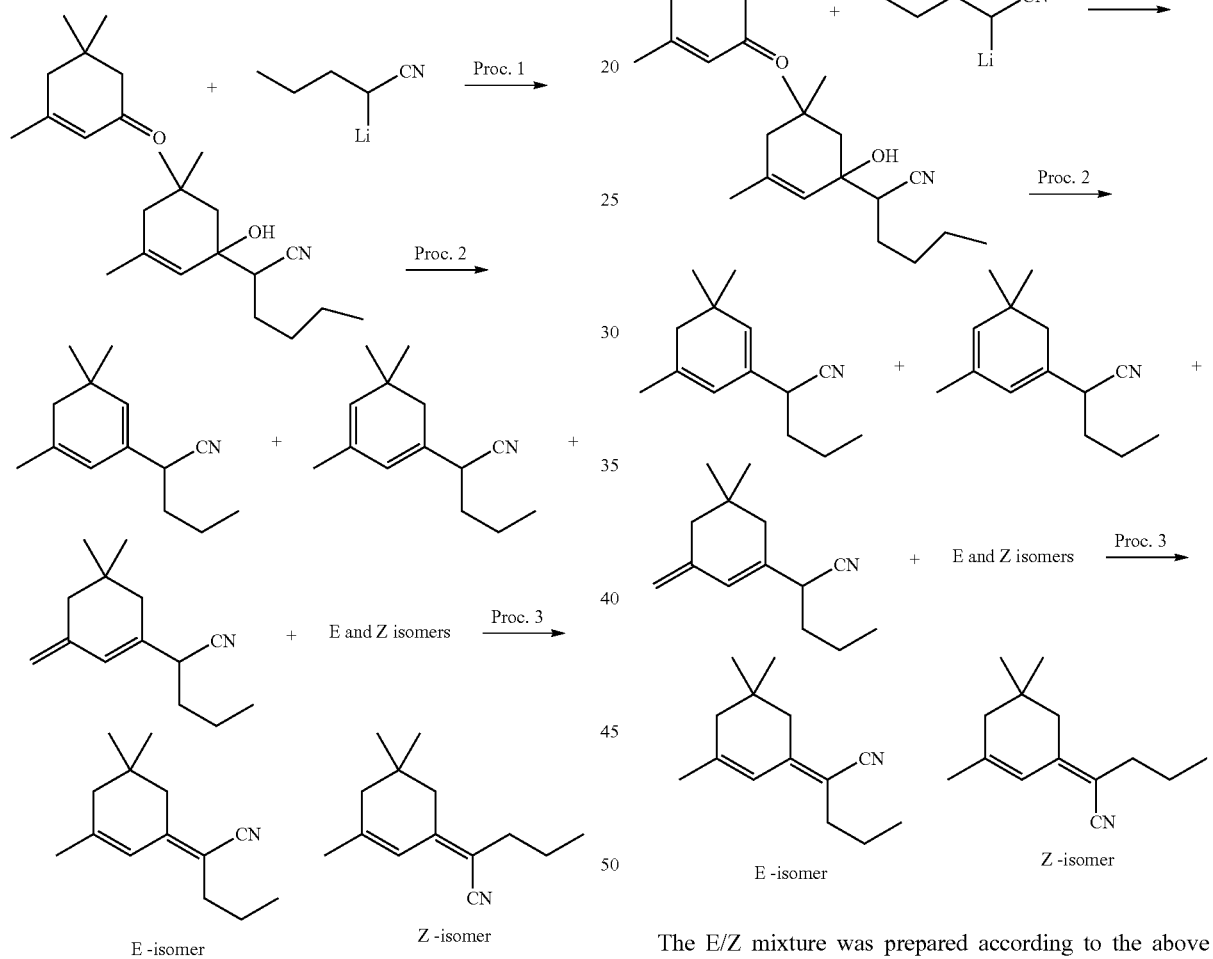

E-isomer          Z-isomer

The E/Z mixture is prepared according to the above scheme, following the General Procedures 1, 2, and 3. For the isomerization (General Procedure 3) 0.18 g of the five component mixture produced by General Procedure 2 is refluxed for 3 h in 10 mL of toluene containing a catalytic amount of TsOH. The crude product is purified by chromatography to yield 0.08 g of a colorless oil.

$^1$H NMR (400 MHz, CDCl$_3$) δ ppm 6.44 (dd, J=2.90, 1.43 Hz, 1H), 6.19-6.18 (m, 1H), 2.34 (s, 1H), 2.23 (td, J=18.47, 7.54, 7.54 Hz, 2H), 2.10 (s, 1H), 1.95 (d, J=7.78 Hz, 2H), 1.85-1.81 (m, 3H), 1.55 (dt, J=7.43, 7.37, 1.81 Hz, 2H), 0.93 (m, 9H)

$^{13}$C NMR (400 MHz, CDCl$_3$) δ ppm 150 7, 149.6, 145.8, 144.2, 121.9, 118.4, 105.6, 45.3, 44.8, 43.4, 39.4, 31.2, 31.0, 30.5, 28.2, 27.9, 24.6, 24.2, 21.9, 21.8, 13.4, 13.3

The 5:4 E:Z mixture is determined by comparison of the integration of the peaks at 6.44 and 6.19 ppm due to the alkene hydrogens.

Example 3

Preparation of the E/Z mixture of another preferred compound of the present invention (3-methyl-2-(3,5,5-trimethylcyclohex-2-en-1-ylidene)butanenitrile) is shown and described below.

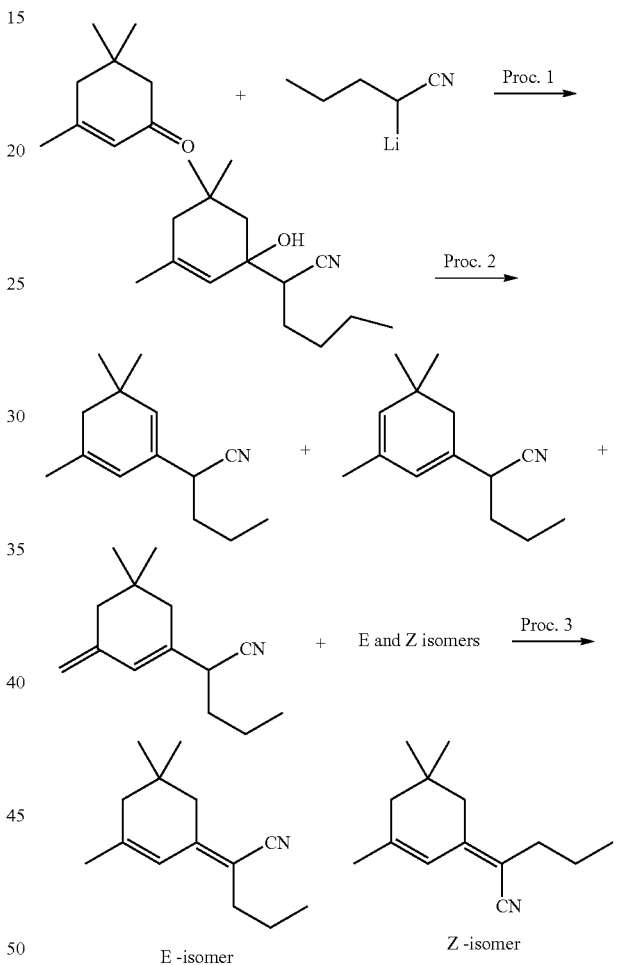

E-isomer          Z-isomer

The E/Z mixture was prepared according to the above scheme following the General Procedures 1, 2, and 3. For the isomerization (General Procedure 3) 0.05 g of the five component mixture produced by General Procedure 2 is refluxed for 3 h in 10 mL of toluene containing a catalytic amount of TsOH. The crude product is purified by chromatography to yield 0.04 g of a colorless oil.

$^1$H NMR (400 MHz, CDCl$_3$) δ ppm 6.43 (d, J=1.41 Hz, 1H), 6.24 (d, J=1.27 Hz, 1H), 2.99-2.89 (m, 1H), 2.88-2.72 (m, 1H), 1.96 (d, J=7.25 Hz, 2H), 1.84 (d, J=3.22 Hz, 2H), 1.12 (dd, J=6.79, 2.00 Hz, 6H), 2.34 (s, 3H), 2.14 (s, 3H), 0.93 (s, 6H)

$^{13}$C NMR (400 MHz, CDCl$_3$) δ ppm 148.9, 147.7, 145.8, 144.3, 122.2, 118.7, 118.4, 117.9, 113.1, 45.5, 44.9, 43.6, 39.4, 31.2, 31.0, 28.2, 27.9, 27.1, 26.6, 24.6, 24.2, 21.7, 21.6

The 2:1 E:Z which was determined by comparison of the integration of the peaks at 6.43 and 6.24 ppm due to the alkene hydrogens.

Example 4

Preparation of the E/Z mixture of another preferred compound of the present invention (2-cyclopropyl-2-(3,5,5-trimethylcyclohex-2-en-1-ylidene)acetonitrile) is described below.

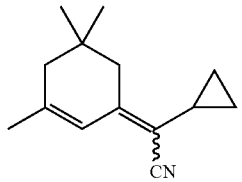

Chemical Formula: C$_{14}$H$_{19}$N
Exact Mass: 201.2

The E/Z mixture is prepared according to the above scheme following the General Procedures 1, 2, and 3. For the isomerization (General Procedure 3) 0.1 g of the five component mixture produced by General Procedure 2 is refluxed for 3 h in 10 mL of toluene containing a catalytic amount of TsOH. The crude product is purified by chromatography to yield 0.09 g of colourless oil.

$^1$H NMR (400 MHz, CDCl$_3$) δ ppm 6.44 (dd, J=2.97, 1.48 Hz, 1H), 6.40 (dd, J=2.94, 1.47 Hz, 1H), 2.27 (s, 3H), 2.33 (d, J=6.00 Hz, 2H), 1.96 (d, J=9.26 Hz, 2H), 1.84 (dd, J=13.25, 0.96 Hz, 3H), 0.93 (d, J=6.06 Hz, 6H), 0.86-0.80 (m, 2H), 0.69 (m, 2H)

$^{13}$C NMR (400 MHz, CDCl$_3$) δ ppm 151.7, 150.3, 145.9, 144.0, 137.8, 129.0, 128.2, 125.3, 122.1, 119.1, 118.5, 117.6, 108.1, 108.0, 45.5, 44.9, 43.6, 39.9, 31.3, 31.1, 28.3, 28.0, 24.7, 24.3, 21.4, 9.7, 9.1, 7.0, 6.9

The 1:1 E:Z is determined by comparison of the integration of the peaks at 6.44 and 6.40 ppm due to the alkene hydrogens.

Example 5

Preparation of the E/Z mixture of another preferred compound of the present invention (2-(3-methylcyclohex-2-en-1-ylidene)propionitrile) is described below.

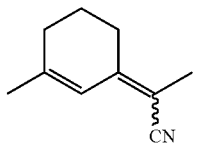

Chemical Formula: C$_{10}$H$_{13}$N
Exact Mass: 147.1

The E/Z mixture is prepared according to the above scheme following the General Procedures 1, 2, and 3. For the isomerization (General Procedure 3) 1.04 g of the five component mixture produced by General Procedure 2 is refluxed for 3 h in 10 mL of toluene containing a catalytic amount of TsOH. The crude product is purified by chromatography to yield 0.50 g of colourless oil.

$^1$H NMR (400 MHz, CDCl$_3$) δ ppm 6.58-6.33 (m, 1H), 6.16 (dd, J=2.90, 1.49 Hz, 1H), 3.74 (s, 1H), 3.42 (s, 1H), 1.72 (m)

$^{13}$C NMR (400 MHz, CDCl$_3$) δ ppm 190.3, 188.8, 42.5, 30.0, 29.7, 29.6, 29.6, 24.7, 24.4, 24.3, 23.0, 22.7, 21.7, 18.4

The 1:1 E:Z mixture is determined by comparison of the integration of the peaks at 6.65 and 6.16 ppm due to the alkene hydrogens.

Example 6

Preparation of the E/Z mixture of another preferred compound of the present invention (2-(4,4-dimethylcyclohex-2-3nen-1-ylidenepropanenotrile) is described below.

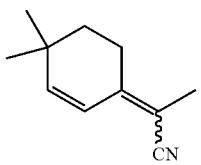

Chemical Formula: C$_{11}$H$_{15}$N
Exact Mass: 161.1

The E/Z mixture is prepared according to the above scheme following the General Procedures 1, 2, and 3. For the isomerization (General Procedure 3) 0.04 g of the flushed material from the General Procedure 2 was refluxed for 3 h in 10 mL of toluene containing a catalytic amount of TsOH. The crude product is purified by chromatography to yield 0.04 g of colourless oil.

$^1$H NMR (400 MHz, CDCl$_3$) δ ppm 6.48 (d, J=9.98 Hz, 1H), 6.23 (d, J=10.07 Hz, 1H), 5.89 (t, J=10.05, 10.05 Hz, 1H), 2.68-2.61 (m, 2H), 2.43-2.38 (m, 2H), 1.91 (s, 3H), 1.60-1.52 (m, 2H), 1.04 (d, J=3.91 Hz, 1H)

The 1:1 E:Z mixture is determined by comparison of the integration of the peaks at 6.48 and 6.23 ppm due to the alkene hydrogens.

Example 7

Preparation of the E/Z mixture of another preferred compound of the present invention is shown and described below.

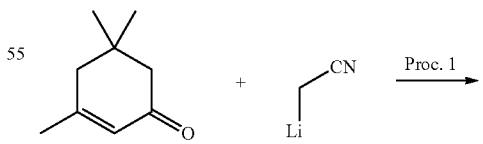

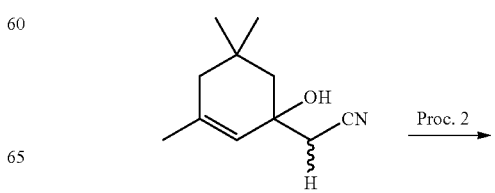

-continued

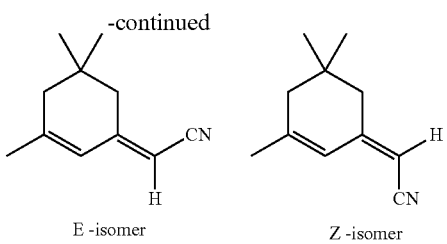

E-isomer    Z-isomer

The E/Z mixture is prepared according to the above scheme following the General Procedures 1 and 2. For the dehydration (General Procedure 2) 0.62 g of the coupling product obtained from General Procedure 1 is stirred for 1 h in 10 mL of toluene containing a catalytic amount of TsOH. The crude product is purified by chromatography to yield a pale yellow oil (0.53 g, 92%, Rf=0.74 in 7:3 Hexanes:EtOAc).

$^1$H NMR (400 MHz, CDCl$_3$) δ ppm 6.37-6.32 (m, 0.5H), 5.96-5.85 (m, 0.4H), 4.88 (s, 0.4H), 4.77 (d, J=0.6 Hz, 0.5H), 2.26 (d, J=1.5 Hz, 1H), 2.04 (d, J=1.5 Hz, 1H), 1.90 (d, J=0.8 Hz, 2H), 1.77 (d, J=16.0 Hz, 3H), 0.85 (d, J=11.8 Hz, 6H).

HRMS: Calculated for $C_{11}H_{15}N$=161.24350, found=161.24054.

The 5:4 E:Z mixture is determined by comparison of the integration of the peaks at 4.9 and 4.7 ppm due to the alkene hydrogens.

The compounds described in the above examples display activity in in vitro and in vivo assays that track brain electrical activity. A first assay is done using voltage sensitive dye imaging. This is done on isolated rat brain slices kept viable in artificial cerebral spinal fluid (ACSF). Electrically stimulating the slice activates the neural assemblies therein. A voltage sensitive dye, such as, di-4-ANEPPS, is incubated with a brain slice for 1 hour in a suitable solution that enhances the dye penetration into the tissue. The dye reacts to changes in voltage across the cell membrane of the neurons in the brain slice. The example compounds are added to the ACSF at known concentration between 200 nM and 1 µM. The brain slices are then subjected to an electrical stimulus that activates the neurons in the slice. As the dye reacts to the change in voltage, which can be observed and quantified, the degree to which activation of the brain is dampened by the presence of the example compound is evaluated.

The compound of Example 1, exemplified above, was able to suppress activation of the brain slice activity by 65±17% at a concentration of 200 nM. In FIG. 1, the suppression of activity is shown by the reduced amplitude of the fluorescence change in layer II of the piriform cortex of a rat. As shown in FIG. 1, the compound of Example 1 suppressed activation of rat brain slices prepared from the piriform cortex. In A two frames of a camera recording about 2 seconds after the stimulation are shown. The two frames shows the increased excitation of neurons in layer 2 of the piriform cortex in response to a 60 Hz stimulus train delivered through the lateral olfactory tract. In B two traces are shown that quantify the increase in activity over a spot within layer 2, over the course of the entire recording. The compound of Example 1 reduced both amplitude and duration of the response. This is indicative of the compounds ability to suppress brain activity.

In a second assay, the inhibition by the example compounds on the activity of voltage-gated sodium channels is determined using patch clamp electrophysiology. This analysis is done on cultured cortical neurons isolated from rats.

Figure 2:
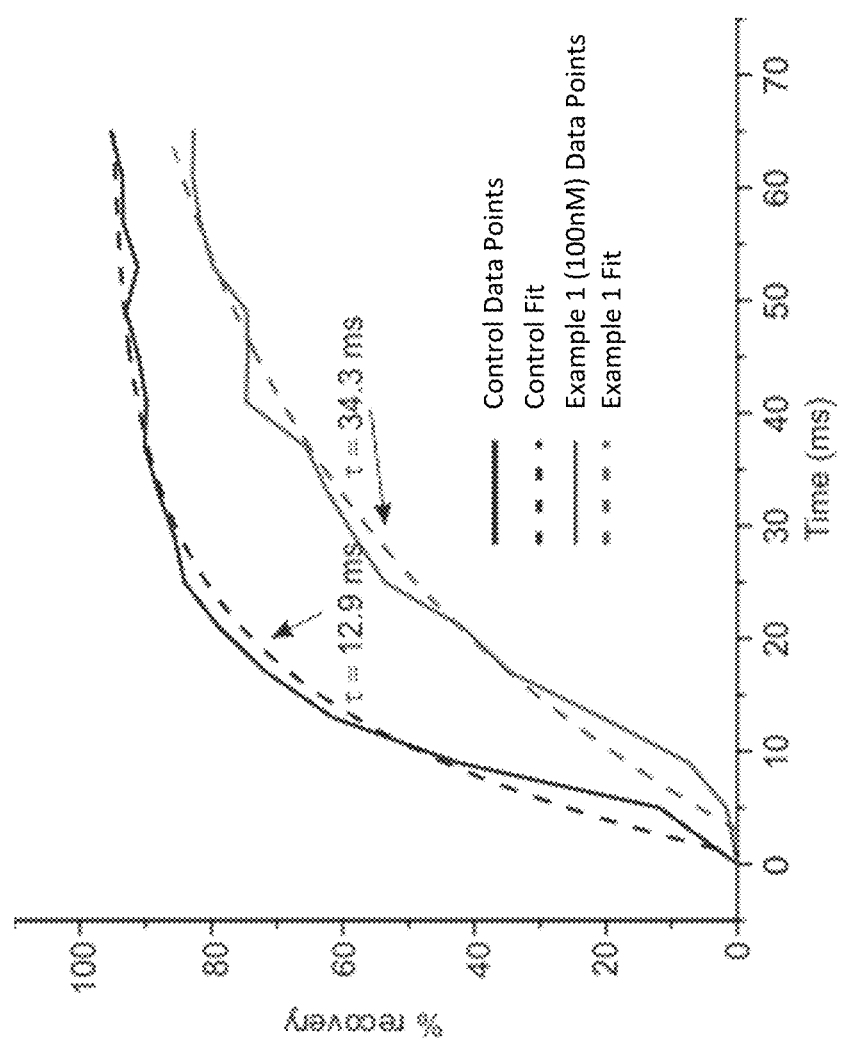
FIG. 2 is a graph showing the recovery time from inactivation of voltage-gated sodium channels in a control sample and in the presence of a preferred compound according to the present invention.

The compound of Example 1 was tested at 100 nM and was shown to slow the recovery of sodium channel inactivation by about 3 fold (13 ms versus 35 ms). As shown in FIG. 2, the upper curves represent the rate of recovery in control recordings done on single neurons in culture. The dotted line shows the single exponential fit of the rate of recovery. This was found to have a time constant of 12.9 ms. The lower solid line represents the data obtained in the presence of the compound of Example 1 (100 nM). The lower dotted line is the single exponential fit of the rate of recovery. In the presence of the compound of Example 1 the rate of recovery was found to be slower having a time constant of 34.3 ms.

The example compounds prolong the time required for voltage-gated sodium channels to recover from a normally occurring inactive state induced by depolarization. At high levels (frequency) of sodium channel activity these compounds are more effective in dampening activity than at low (non-seizure) levels of activity. Thus, the example compounds tend to suppress abnormal brain behavior to a higher degree than normal brain behavior.

A number of embodiments of the present invention have been described. Nevertheless, the embodiments are described herein illustratively and are not meant to limit the scope of the invention, as claimed. Variations of the foregoing embodiments will be evident to a person of ordinary skill and are intended by the inventor to be encompassed by the following claims.

What is claimed is:

1. A method for reducing the severity of convulsant activity, comprising administering to a subject in need of reducing the severity of convulsant activity a therapeutically effective amount of a compound represented by the following formula (I):

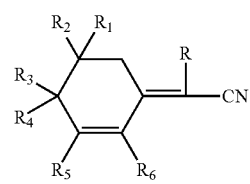

wherein,

R=H, CH$_3$, linear or branched C$_2$ to C$_6$, cC$_3$H$_5$, cC$_5$H$_9$, cC$_6$H$_{11}$, CH=CH$_2$, or CH$_2$-phenyl, R$_1$=R$_2$=H or CH$_3$, R$_3$=R$_4$=H or CH$_3$, R$_5$=H, CH$_3$, OCH$_3$, OCH$_2$-phenyl, Cl, or Br, and R$_6$=H or CH$_3$.

2. The method of claim 1, wherein R=H, CH$_3$, linear or branched C$_2$ to C$_6$, cC$_3$H$_5$, cC$_5$H$_9$, or cC$_6$H$_{11}$.

3. The method of claim 2, wherein R$_5$=H or CH$_3$.

4. The method of claim 3, wherein R=H, CH$_3$, or linear or branched C$_2$ to C$_6$.

5. The method of claim 4, wherein R=H or CH$_3$.

6. The method of claim 1, wherein the compound represented by the formula (I) is a compound represented by the following formula:

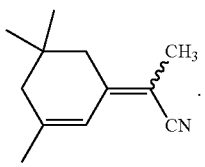

7. The method of claim 1, wherein the compound represented by the formula (I) is 2-(3,5,5-trimethylcyclohex-2-en-1-ylidene)pentanenitrile.

8. The method of claim 1, wherein the compound represented by the formula (I) is 3-methyl-2-(3,5,5-trimethylcyclohex-2-en-1-ylidene)butanenitrile.

9. The method of claim 1, wherein the compound represented by the formula (I) is a compound represented by the following formula:

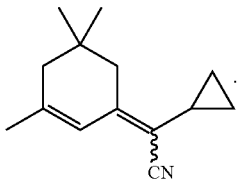

10. The method of claim 1, wherein the compound represented by the formula (I) is a compound represented by the following formula:

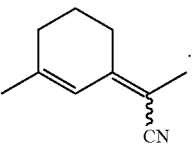

11. The method of claim 1, wherein the compound represented by the formula (I) is a compound represented by the following formula:

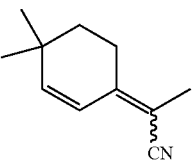

12. The method of claim 1, wherein the compound represented by the formula (I) is a compound represented by the following formula:

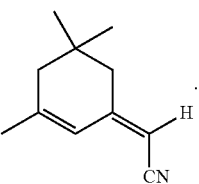

* * * * *